United States Patent [19]
Cianciara

[11] Patent Number: 5,747,668
[45] Date of Patent: May 5, 1998

[54] DIAGNOSTIC PROCESS FOR AN EXHAUST GAS SENSOR

[75] Inventor: Wojciech Cianciara, Gruenthal, Germany

[73] Assignee: Siemens Aktiengesellschaft, Munich, Germany

[21] Appl. No.: 699,224

[22] Filed: Aug. 19, 1996

[30] Foreign Application Priority Data

Aug. 17, 1995 [DE] Germany .................. 195 30 316.4

[51] Int. Cl.$^6$ ..................................................... F02B 77/08
[52] U.S. Cl. ..................................................... 73/1.06
[58] Field of Search .................... 73/1 G, 118.1; 13/1.06

[56] References Cited

U.S. PATENT DOCUMENTS

| 5,357,791 | 10/1994 | Gee et al. ............... | 73/118.1 |
| 5,488,858 | 2/1996 | Achleitner ............... | 73/118.1 |
| 5,526,798 | 6/1996 | Seki ....................... | 73/118.1 |

FOREIGN PATENT DOCUMENTS

| 25 30 849 | 4/1976 | Germany . |
| 27 58 319 | 4/1987 | Germany . |
| 4338342A1 | 5/1995 | Germany . |
| 90/09517 | 8/1990 | WIPO . |

*Primary Examiner*—Robert Raevis
*Attorney, Agent, or Firm*—Herbert L. Lerner; Laurence A. Greenberg

[57] ABSTRACT

A process for monitoring the functioning of an exhaust gas sensor disposed in a mixture-regulating circuit of an internal combustion engine includes outputting either a rich voltage representing a rich mixture composition or a lean voltage representing a lean mixture composition as a function of a composition of a mixture to be supplied to the engine, and using a behavior of the voltages during engine operation as a criterion for evaluating the functioning of the exhaust gas sensor. The temperature of an exhaust gas sensor is ascertained and compared with a temperature threshold value. If the temperature threshold value is exceeded, monitoring is performed to determine if that status is maintained for a predetermined period of time or number of cycles. A value occurring for a rich voltage or a lean voltage is detected and compared with a diagnostic value if the conditions are met. It is concluded that the exhaust gas sensor is superannuated, if the diagnostic threshold is not attained.

14 Claims, 2 Drawing Sheets

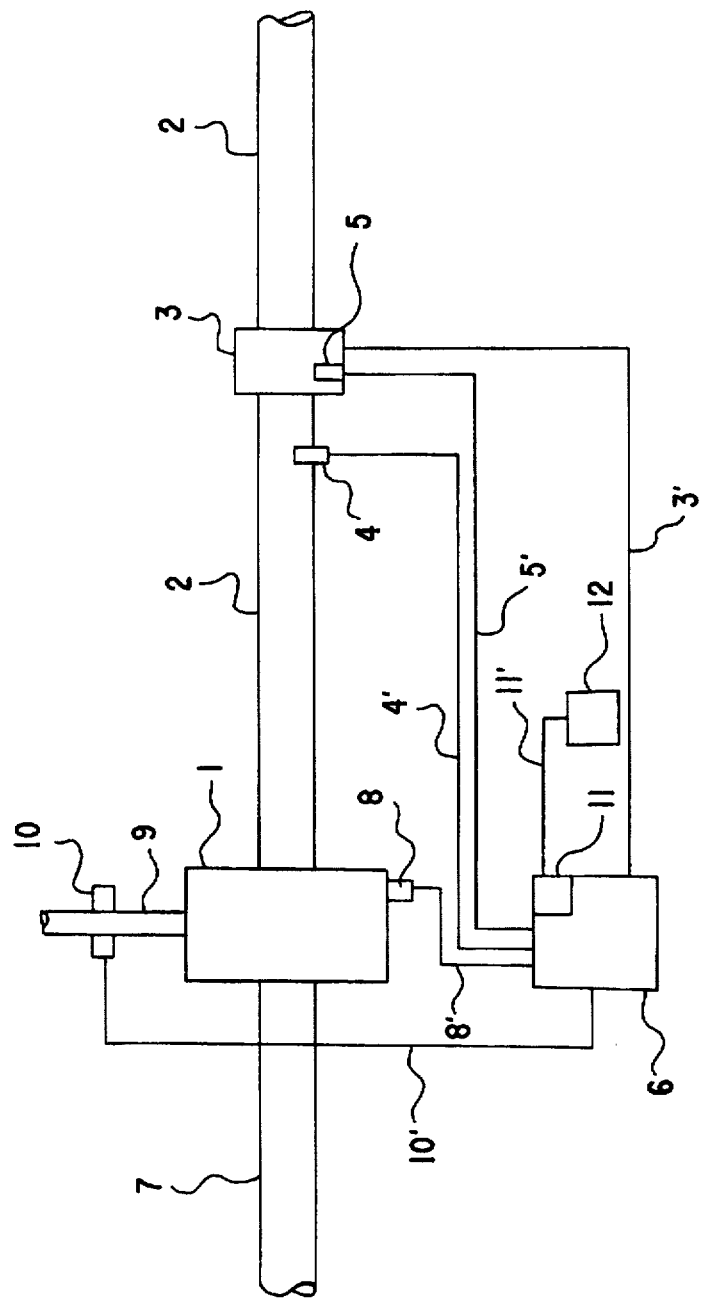

DIAGNOSTIC PROCESS FOR AN EXHAUST GAS SENSOR

BACKGROUND OF THE INVENTION

Field of the Invention

The invention relates to a process for monitoring the functioning of an exhaust gas sensor disposed in the mixture-regulating circuit of an internal combustion engine, which includes outputting either a rich voltage representing a rich mixture composition or a lean voltage representing a lean mixture composition as a function of the composition of a mixture to be supplied to the engine, and using the behavior of those voltages during engine operation as a criterion for evaluating the functioning of the exhaust gas sensor.

In order to lower fuel consumption and to minimize the proportion of pollutants in the exhaust gas of an internal combustion engine, it is important to keep the fuel-air ratio of the mixture to be supplied to the engine combustion chambers at an optimal, previously fixed value. What is known as lambda control is used for that purpose. Lambda control in combination with a three-way catalyst is an effective exhaust gas cleaning process for internal combustion engines. An oxygen sensor, referred to below as a lambda sensor, which is disposed in the engine intake tube, furnishes a signal that is dependent on the residual oxygen content in the exhaust gas. That output signal is further processed in a lambda control system in such a way that a mixture preparation system, such as a carburetor or fuel injection system, produces an optimal fuel-air mixture, thereby enabling virtually complete combustion ($\lambda=1$).

The lambda sensors used in such control systems are constructed in such a way that when the fuel-air mixture is rich ($\lambda<1$), they output a high or so-called rich voltage, while for a lean fuel-air mixture ($\lambda>1$) they produce a low or so-called lean voltage. However, the reverse association between the voltage and the mixture is also possible. The transition from the high to the lower voltage and vice versa occurs virtually abruptly at the air number $\lambda=1$.

A disadvantage of such a lambda control system is that the output signal of the lambda sensor is highly temperature-dependent, and the output characteristic curve varies as a consequence of aging and wear. The rich and lean voltages, especially, shift in response to those factors.

Unless the drift in the output signal resulting from natural aging caused by the extreme temperature fluctuations from about $-40°$ C. to $+950°$ C. and by the aggressive atmosphere in the exhaust gas, is taken into account in the control of the fuel-air ratio, the result is an increase in pollutant emissions from the engine.

German Patent DE 27 58 319 C2 has disclosed an apparatus for regulating the fuel-air ratio of an internal combustion engine equipped with an exhaust gas sensor, in which the output voltage of the exhaust gas sensor is compared with a variable reference voltage, and a control signal for varying the fuel-air delivery is obtained from the comparison. To that end, a circuit for generating the variable reference voltage with a voltage follower is provided, which generates first and second signals that reproduce upper and lower envelope curves for the instantaneous maximum and minimum peak voltages in the output voltage of the exhaust gas sensor. A predetermined ratio between those two voltages produces the reference voltage, which is adapted to the aging of the exhaust gas sensor. Since the two envelope curves of the maximum and minimum peak voltages of the output signal of the exhaust gas sensor each vary in the same way as a function of the temperature and the aging of the exhaust gas sensor, the reference voltage is essentially independent of temperature changes and aging of the exhaust gas sensor.

German Published, Non-Prosecuted Patent Application DE 25 30 849 A1 describes a detector system for ascertaining the failure of an exhaust gas sensor in the exhaust gas system of an internal combustion engine that does not require particular engine operating conditions, except for the prerequisite that the sensor be at its operating temperature. One characteristic for the quality of the sensor is if the transition from a high voltage level to a low voltage level occurs within a predetermined interval when the exhaust gas is changed from a rich to a lean fuel mixture. If the output signal of the sensor does not pass through that transition within a predetermined time period, specifically the predetermined interval, then that is a characteristic indication that the sensor has failed, and a warning signal is issued.

SUMMARY OF THE INVENTION

It is accordingly an object of the invention to provide a diagnostic process for an exhaust gas sensor, which overcomes the hereinafore-mentioned disadvantages of the heretofore-known methods of this general type and with the aid of which superannuated or aged exhaust gas sensors can be detected in a simple way.

With the foregoing and other objects in view there is provided, in accordance with the invention, a process for monitoring the functioning of an exhaust gas sensor disposed in a mixture-regulating circuit of an internal combustion engine, which comprises ascertaining a temperature of an exhaust gas sensor and comparing the temperature of the exhaust gas sensor with a temperature threshold value; if the temperature threshold value is exceeded, monitoring to determine if the temperature threshold value remains exceeded for a predetermined period of time or number of cycles; outputting either a rich voltage representing a rich mixture composition or a lean voltage representing a lean mixture composition from the exhaust gas sensor as a function of a composition of a mixture to be supplied to the engine; and using a behavior of the voltages during engine operation as a criterion for evaluating the functioning of the exhaust gas sensor by detecting and comparing a value occurring for a rich voltage or a lean voltage with a diagnostic value if the conditions are met, and concluding that the exhaust gas sensor is superannuated, if the diagnostic threshold is not attained.

In accordance with another mode of the invention, there is provided a process which comprises deriving the temperature threshold value from engine operating parameters, in particular from rpm and load parameters.

In accordance with a further mode of the invention, there is provided a process which comprises ascertaining the temperature threshold experimentally by driving tests.

In accordance with an added mode of the invention, there is provided a process which comprises indicating an outcome of the monitoring acoustically and/or optically.

In accordance with an additional mode of the invention, there is provided a process which comprises storing an outcome of the monitoring in a diagnostic memory of a control unit of the engine.

In accordance with a concomitant mode of the invention, there is provided a process which comprises indicating or storing the outcome in memory only after a statistical evaluation of a plurality of successive monitoring operations.

With the aid of the process of the invention, it is possible to detect superannuated exhaust gas sensors in a simple manner and to indicate the outcome to the vehicle driver directly in the form of a warning signal and/or store the outcome of the monitoring in a diagnostic memory, so that maintenance steps, and in particular the replacement of the superannuated exhaust gas sensors, can be initiated.

Other features which are considered as characteristic for the invention are set forth in the appended claims.

Although the invention is illustrated and described herein as embodied in a diagnostic process for an exhaust gas sensor, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWINGS

FIG. 3 is a schematic diagram of a mixture-regulating circuit of an internal combustion engine having an exhaust gas sensor.

DESCRIPTION OF THE PREFERRED EMBODIMENTS

Figure 1:
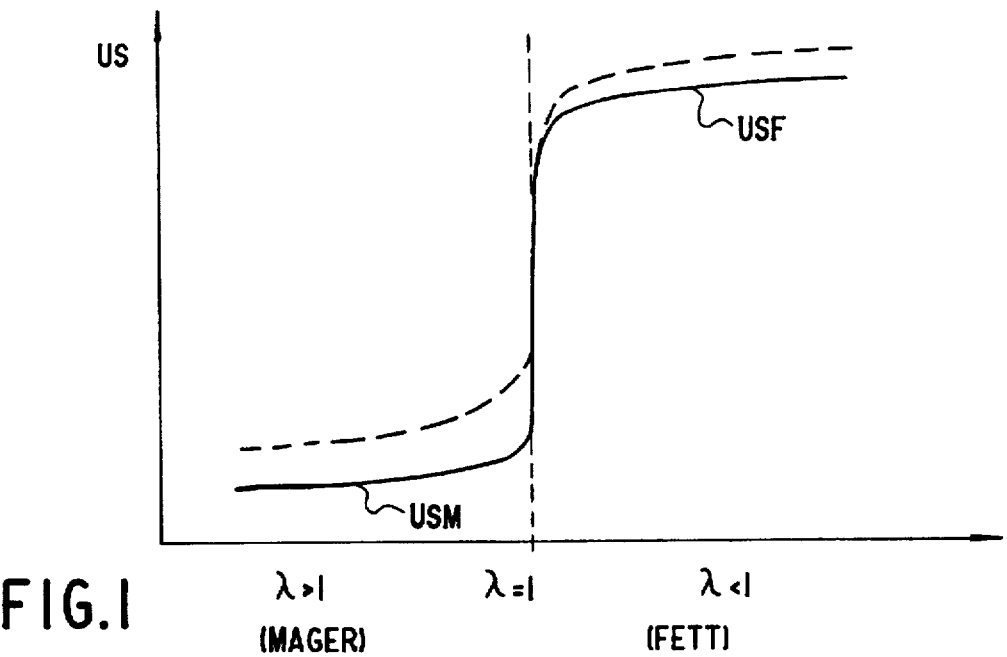
FIG. 1 is a graph of an output characteristic curve of an exhaust gas sensor, plotted as a function of air number.

Referring now to the figures of the drawings in detail and first, particularly, to FIG. 3 thereof, there is seen an engine 1 having a mixture-regulating circuit. The engine has an intake pipe 7 and an exhaust pipe 2 with a temperature sensor 4. An exhaust gas sensor 3 which is connected to the exhaust pipe 2 has a temperature sensor 5. An engine controller 6 is connected over a line 3' to the sensor 3, over a line 4' to the sensor 4 and over a line 5' to the sensor 5. The engine 1 has an engine rpm sensor 8 connected to the engine controller 6 over a line 8'. An output shaft 9 of the engine 1 has an engine load sensor 10 which is connected over a line 10' to the engine controller 6. The engine controller 6 contains a diagnostic memory 11 which is connected over a line 11' to an acoustical and/or optical warning device 12.

FIG. 1 shows a relationship between an output voltage US and an air number λ of an exhaust gas sensor with a step-change characteristic at a certain temperature. When a fuel-air mixture is lean, the exhaust gas sensor outputs a low voltage, namely a lean voltage USM, and when the fuel-air mixture is rich it outputs a high voltage, namely a rich voltage USF, that is higher than the lean voltage. A transition between the two voltage values USF, USM takes place virtually abruptly, because at slightly higher air numbers, uncombusted oxygen is suddenly present in the exhaust gas.

The output voltage at a higher temperature is also plotted in FIG. 1 and represented by a dashed line. It can be seen from this merely qualitatively illustrated course that the lean voltage USM exhibits a greater temperature dependency than does the rich voltage. Therefore, that portion of the output characteristic curve which describes the fuel-air ratio in the lean range is used to diagnose the aging of the exhaust gas sensor.

The effect of aging on the output signal US of the exhaust gas sensor will be described below in conjunction with FIG. 2 while taking the lean voltage USM as an example. A solid line A indicates the course of the lean voltage USM in a new exhaust gas sensor that has not yet been exposed to the exhaust gas stream, and a dashed line B shows the course for a greatly superannuated exhaust gas sensor that accordingly no longer has the requisite control accuracy. In each case the lean voltage USM is plotted as a function of the temperature T of the exhaust gas sensor. A threshold value for the output voltage which is referred to below as a diagnostic voltage UDIAG, and a threshold value for the temperature which is referred to below as a temperature threshold value T1, are also plotted in FIG. 2.

The monitoring of the exhaust gas sensor is carried out as follows:

Through the use of measurements of such engine operating parameters as rpm and load, it must be assured that the exhaust gas temperature and thus the temperature of the exhaust gas sensor protruding into the exhaust gas stream, has a value that is greater than the temperature threshold value T1. This value T1 is ascertained experimentally for a given engine by driving tests or on a test bench and is affected essentially by the structure of the engine and the exhaust gas sensor, as well as by the installation site and therefore the distance of the exhaust gas sensor from the engine.

Along with the possibility of deriving the attainment of the temperature threshold value T1 indirectly from engine operating parameters, it is alternatively also possible, for detecting the value T1, to provide a temperature sensor that protrudes into the exhaust gas stream or is integrated with the exhaust gas sensor.

Figure 2:
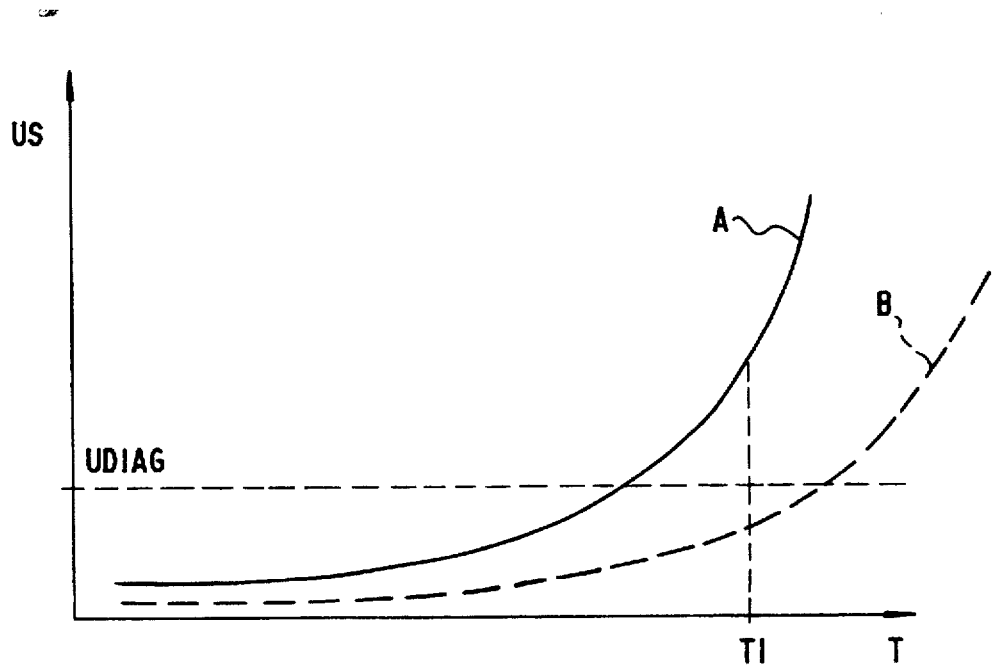
FIG. 2 is a graph showing a portion of the output characteristic curve of the exhaust gas sensor, plotted as a function of temperature.

Since the temperature-dependent drift of the lean voltage USM increases as the temperature T rises in FIG. 2, for the sake of accurate evaluation of the sensor voltage the temperature threshold value Ti is chosen to be relatively high, so that it is reached only in certain operating states of the engine, such as at high load and high rpm.

If it is certain that the temperature threshold value T1 has been reached, which can be detected, for instance, from the exceeding of an rpm and load threshold, and if this operating state also persists over a predetermined period of time or number of cycles, then a monitoring operation is performed to learn whether or not the lean voltage USM has exceeded the diagnostic value UDIAG. If not, then the finding is made that the exhaust gas sensor has aged to such an extent that it should be replaced. This information can be imparted to the vehicle driver directly, acoustically and/or optically, through the use of a warning device, and/or an error diagnosis can be entered into a diagnostic memory of an engine control unit.

In order to preclude possible incorrect diagnoses, it is also possible to not yet indicate or memorize the first negative outcome of the monitoring, but instead to perform monitoring a plurality of times and to store the outcome in memory only after a statistical evaluation has been performed.

I claim:

1. A process for monitoring the functioning of an exhaust gas sensor disposed in a mixture-regulating circuit of an internal combustion engine, which comprises:

ascertaining a temperature of an exhaust gas sensor and comparing the temperature of the exhaust gas sensor with a temperature threshold value;

if, as a first condition, the temperature threshold value is exceeded, monitoring to determine if the temperature threshold value, as a second condition, remains exceeded for a predetermined period of time or number of cycles;

outputting either a rich voltage representing a rich mixture composition or a lean voltage representing a lean mixture composition from the exhaust gas sensor as a function of a composition of a mixture to be supplied to the engine; and using a behavior of the voltages during engine operation as a criterion for evaluating the functioning of the exhaust gas sensor by:

detecting and comparing a value occurring for a rich voltage or a lean voltage with a diagnostic threshold value if the first and second conditions are met, and concluding that the exhaust gas sensor is superannuated, if the diagnostic threshold value is not attained.

2. The process according to claim 1, which comprises deriving the temperature threshold value from engine operating parameters.

3. The process according to claim 1, which comprises deriving the temperature threshold value from rpm parameters.

4. The process according to claim 1, which comprises deriving the temperature threshold value from load parameters.

5. The process according to claim 1, which comprises ascertaining the temperature threshold experimentally by driving tests.

6. The process according to claim 1, which comprises indicating an outcome of the monitoring acoustically.

7. The process according to claim 6, which comprises indicating the outcome after a statistical evaluation of a plurality of successive monitoring operations.

8. The process according to claim 1, which comprises indicating an outcome of the monitoring optically.

9. The process according to claim 8, which comprises indicating the outcome after a statistical evaluation of a plurality of successive monitoring operations.

10. The process according to claim 1, which comprises indicating an outcome of the monitoring acoustically and optically.

11. The process according to claim 10, which comprises indicating the outcome after a statistical evaluation of a plurality of successive monitoring operations.

12. The process according to claim 1, which comprises storing an outcome of the monitoring in a diagnostic memory of a control unit of the engine.

13. The process according to claim 12, which comprises storing the outcome in memory after a statistical evaluation of a plurality of successive monitoring operations.

14. A process for monitoring the functioning of an exhaust gas sensor disposed in a mixture-regulating circuit of an internal combustion engine, which comprises:

ascertaining a temperature of an exhaust gas sensor and comparing the temperature of the exhaust gas sensor with a temperature threshold value;

defining a first condition in which the temperature of the exhaust gas sensor exceeds the threshold value;

if the first condition is met, defining a second condition in which the temperature of the exhaust gas sensor remains above the temperature threshold value for a predetermined period of time or number of cycles;

outputting either a rich voltage representing a rich mixture composition or a lean voltage representing a lean mixture composition from the exhaust gas sensor as a function of a composition of a mixture to be supplied to the engine; and if the first and second conditions are met during engine operation, evaluating the functioning of the exhaust gas sensor by:

detecting and comparing a value occurring for a rich voltage or a lean voltage with a respective diagnostic threshold value, and concluding that the exhaust gas sensor is superannuated, if the respective diagnostic threshold value is not attained.

* * * * *